United States Patent [19]

Matsumura et al.

[11] 4,211,866
[45] Jul. 8, 1980

[54] ACYL DERIVATIVES OF 2-[3-(2-CHLOROETHYL)-3-NITROSOUREIDO]-2-DEOXY-D-GLUCOPYRANOSE

[75] Inventors: Shingo Matsumura; Masakuni Ozaki; Hisao Watanabe; Hiroyuki Kuroda; Teruya Nakamura; Akira Obayashi, all of Kyoto, Japan

[73] Assignees: Nippon Shinyaku Co., Ltd.; Takara Shuzo Co., Ltd., both of Japan

[21] Appl. No.: 948,169

[22] Filed: Oct. 3, 1978

[30] Foreign Application Priority Data

Oct. 3, 1977 [JP] Japan ................................ 52/119270

[51] Int. Cl.² .................................................. C07H 5/06
[52] U.S. Cl. ........................................ 536/53; 424/180; 536/4; 536/119
[58] Field of Search ............................ 536/4, 53, 119

[56] References Cited

U.S. PATENT DOCUMENTS 4,057,684  11/1977  Kimura et al. ......................... 536/53

*Primary Examiner*—Johnnie R. Brown
*Attorney, Agent, or Firm*—Jacobs & Jacobs

[57] ABSTRACT

Acylated derivatives of 2-[3-(2-chloroethyl)-3-nitrosoureido]-2-deoxy-D-glucopyranose have antitumor activity.

6 Claims, No Drawings

ACYL DERIVATIVES OF 2-[3-(2-CHLOROETHYL)-3-NITROSOUREIDO]-2-DEOXY-D-GLUCOPYRANOSE

DETAILED DESCRIPTION

This invention relates to acyl derivatives of 2-[3-(2-chloroethyl)-3-nitrosoureido]-2-deoxy-D-glucopyranose of the formula:

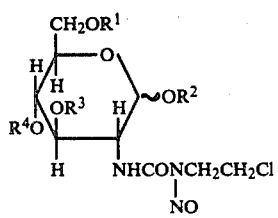

wherein $R^1$, $R^2$, $R^3$ and $R^4$ are the same or different and each is selected from the group consisting of hydrogen and $—CO(C_nH_{2n})CH_3$ in which n has a value of from 8 to 16, at least one of $R^1$, $R^2$, $R^3$ and $R^4$ being other than hydrogen.

The acyl derivatives of 2-[3-(2-chloroethyl)-3-nitrosoureido]-2-deoxy-D-glucopyranose of the invention have significant antitumor and antileukemic activity and are characterized not only by a reduced impairment of hematopoietic function but also by a significant reduction in acute toxicity, e.g., a minimum of deleterious effect on the kidney, spleen, liver and other organs.

The antitumor activity and acute toxicity of the acyl derivatives of 2-[3-(2-chloroethyl)-3-nitrosoureido]-2-deoxy-D-glucopyranose according to this invention can be conveniently observed in recognized animal models. 1,000,000 cells of mouse lymphatic leukemia P-388 were intraperitoneally transplanted into each mouse (SLC-BDF₁, male, 18g±1 g, 5 weeks old). After 24 hours and thereafter at intervals of 24 hours, a predetermined amount of an acyl derivative of 2-[3-(2-chloroethyl)-3-nitro-soureido]-2-deoxy-D-glucopyramose was intraperitoneally administered for a total of 9 doses. The mice were reared under observation. The results are set forth in Table 1.

Table 1

| | Antileukemic activity against Leukemia P-388 | | |
|---|---|---|---|
| Compound | Dosage mg/Kg/dose | Median survival time, in days | Increase of Life Span (%) |
| 2-[3-(2-Chloroethyl)-3-nitrosoureido]-2-deoxy-D-glucopyranose (chlorozotocin) | 1.0 | 18.8 | 84.3 |
| | 0.5 | 16.3 | 59.8 |
| | 0.25 | 14.5 | 42.2 |
| | 0.125 | 12.3 | 20.6 |
| Dicaprate | 1.0 | 19.8 | 94.1 |
| | 0.5 | 18.3 | 79.4 |
| | 0.25 | 15.7 | 53.9 |
| | 0.125 | 10.8 | 5.9 |
| Monopalmitate | 1.0 | 17.5 | 71.6 |
| | 0.5 | 16.3 | 59.8 |
| | 0.25 | 15.5 | 52.0 |
| | 0.125 | 14.8 | 45.1 |
| Dipalmitate | 1.0 | 21.0 | 105.9 |
| | 0.5 | 19.3 | 89.2 |
| | 0.25 | 17.8 | 74.5 |
| | 0.125 | 16.5 | 61.8 |
| Monomyristate | 1.0 | 17.8 | 74.5 |
| | 0.5 | 16.0 | 56.9 |
| | 0.25 | 15.5 | 52.0 |

Table 1-continued

| | Antileukemic activity against Leukemia P-388 | | |
|---|---|---|---|
| Compound | Dosage mg/Kg/dose | Median survival time, in days | Increase of Life Span (%) |
| | 0.125 | 14.0 | 37.3 |
| Dimyristate | 1.0 | 20.8 | 103.9 |
| | 0.5 | 19.8 | 94.1 |
| | 0.25 | 17.3 | 69.6 |
| | 0.125 | 15.3 | 50.0 |
| Control (physiological saline) | | 10.2 | 0 |

It can be seen from the above that the acyl derivatives of 2-[3-(2-chloroethyl)-3-nitrosoureido]-2-deoxy-D-glucopyranose have excellent antileukemic activity, the dosed groups showing marked increases in average life span over the control group.

The acute toxicity data also in mice for the compounds of this invention are shown in Table 2.

Table 2

| Acute toxicities in mice (male, ddy). | |
|---|---|
| Compound | $LD_{50}$* |
| Chlorozotocin | 45–47 mg/Kg |
| Monocaprate | 17.7 |
| Dicaprate | 141.4 |
| Tricaprate | >400 |
| Monomyristate | 61.5 |
| Dimyristate | >800 |
| Trimyristate | >800 |
| Monopalmitate | 162.5 |
| Dipalmitate | >800 |
| Tripalmitate | >800 |
| Monostearate | 187 |
| Distearate | >800 |
| Tristearate | >800 |

*Intraperitoneal administration of a single dose, 7 days survival.

The compounds are administered parenterally or orally in conventional pharmaceutical forms, as for example, solid and liquid oral unit dosage forms such as tablets, capsules, powders, suspensions, solutions, syrups and the like, including sustained release preparations, and fluid injectable forms such as sterile solution and suspensions. The term unit dosage form as used in this specification and the claims refer to physically discrete units to be administered in single or multiple dosage, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in units dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The acyl derivatives of the present invention are palliatives and it will thus be appreciated in view of the nature of the condition being treated that the dose must, in each case, be titrated to the patient, taking into consideration the general condition, age, weight and response desired. As noted above a response can be observed upon administration of as low as about 0.1 mg/kg of body weight per day. In each instance, administration should only be effected utilizing sound professional judgment. The present disclosure is specifically directed at the medical and veterinarian arts, and the allied arts, and should not be construed as a suggestion or recommendation for use by others in the absence of such professional guidance and without compliance with all applicable Federal and state laws.

The compounds of this invention can be produced by several different procedures. More particularly, the compounds of this invention can be obtained, for example by suspending 2-[3-(2-chloroethyl)ureido]-2-deoxy-D-glucopyranose in a suitable solvent such as pyridine, reacting it with a fatty acid halide, preferably a chloride, or a fatty acid anhydride at or below room temperature and reacting the resultant acylation product with a suitable nitrosating agent such as sodium nitrite, either as previously dissolved in water or as directly added in particulate form to the reaction system, in a suitable solvent such as acetic acid at a temperature not exceeding room temperature. Alternatively, 2-[3-(2-chloroethyl)-3-nitrosoureido]-2-deoxy-D-glucopyranose may be reacted with a fatty acid chloride or anhydride. In the transesterification process, the desired compound can be obtained by adding a fatty acid ester to 2-[3-(2-chloroethyl)ureido]-2-deoxy-D-glucopyranose in a suitable solvent such as dimethylformamide and in the presence of potassium carbonate, heating the reaction system and nitrosating the resultant acyl derivative in the same manner as above. When the number of carbon atoms in the fatty acid employed in the reaction is less than 8, the acyl derivative has high acute toxicity and especially the monoacyl derivative has very high toxicity and is undesirable.

The following examples are intended to further describe the procedures for producing the compounds of this invention.

EXAMPLE 1

In 30 ml of pyridine was suspended 1.5 g of 2-[3-(2-chloroethyl)-ureido]-2-deoxy-D-glucopyranose and, under stirring at room temperature, 3.6 g of palmitoyl chloride was added dropwise. After being stirred for one hour, the reaction mixture was poured in ice-water, adjusted to pH 3 with concentrated sulfuric acid and extracted with chloroform. The extract was washed with water, dehydrated and distilled to remove the solvent. To the residue was added 45 cc of acetic acid and, under stirring at room temperature, 1 g of $NaNO_2$ was added. The mixture was stirred for 30 minutes and, after a small amount of water was added, the precipitate was recovered by filtration, rinsed well with water, dried and subjected to silica gel column chromatography (Wakogel ®C-200). Elution with benzene provided the tetraester; with benzene-ethyl acetate (15:1), the triester was obtained; with benzene-ethyl acetate (5:1), the diester was obtained; and with benzene-ethyl acetate (5:2), the monoester was obtained.

(1) 2-[3-(2-chloroethyl-3-nitrosoureidol]-2-deoxy-D-glucopyranose tripalmitate

Yield: 120 mg, m.p. 95°–97° C.; mol. formula $C_{57}H_{106}ClN_3O_{10}$;

Analysis: found (calcd.), % C,66.85(66.57); H, 10.38(10.58); N, 4.08(3.87) IR(KBr, $CM^{-1}$): 3500, 3375, 2920, 2855, 1760, 1740, 1715, 1535, 1495, 1470.

(2) 2-[3-(2-chloroethyl)-3-nitrosoureido]-2-deoxy-D-glucopyranose dipalmitate

Yield 900 mg; m.p. 116°–118° C., mol. formula $C_{41}H_{76}ClN_3O_9$;

Analysis: found (calcd.), % C, 62.13(62.29); H, 9.64(9.69); N 5.20(5.31) IR(KBr, $CM^{-1}$): 3380, 2920, 2855, 1725, 1715, 1550, 1495 1465.

(3) 2-[3-(2-chloroethyl)-3-nitrosoureido]-2-deoxy-D-glucopyranose monopalmitate

Yield 300 mg; m.p. 119° C. (decomp.); mol. formula: $C_{25}H_{46}ClN_3O_8$

Analysis: found(calcd)% C, 54.45(54.30); H, 8.67(8.40); N, 7.67(7.61); IR(KBr, $CM^{-1}$): 3480, 3400, 2925, 2850, 1730, 1690, 1535, 1490, 1465.

(4) 2-[3-(2-chloroethyl)-3-nitrosureido]-2-deoxy-D-glucopyranose tetrapalmitate

Yield 10 mg; m.p. 73°–75° C.; mol. formula: $C_{73}H_{136}ClN_3O_{11}$;

Analysis: found (calcd)% C, 69.01(69.18); H, 10.77(10.82); N, 3.51(3.32); IR(KBr, $CM^{-1}$): 3500, 3380, 2920, 2855, 1780, 1755, 1730, 1715, 1535, 1495, 1470.

EXAMPLE 2

In 20 ml of pyridine was dissolved 1 g of 2-[3-(2-chloroethyl)-3-nitrosoureido]-2-deoxy-D-glucopyranose and, under stirring at room temperature, 2.2 g of palmitoyl chloride was added dropwise. The mixture was stirred for an hour, at the end of which time ethanol and benzene were added. The mixture was concentrated to dryness under reduced pressure at 40° C. and the residue was purified by silica gel column chromatography as in Example 1. This procedure provided the mono-, di- and tripalmitates which, in IR, analysis and melting point, were identical with the corresponding compounds obtained in Example 1.

EXAMPLE 3

In 20 ml of pyridine was suspended 1 g of 2-[3-(2-chloroethyl)ureido]-2-deoxy-D-glucopyranose, and a catalytic amount of p-toluenesulfonic acid was added. Under stirring at room temperature, 3.5 g of palmitic anhydride was dissolved in pyridine was added. The mixture was stirred for 5 hours, at the end of which time the pyridine was distilled off under reduced pressure. To the residue was added ether, the insolubles were filtered off and the ether was distilled off. To the residue was added 30 ml of acetic acid and, under stirring at room temperature, 0.8 of sodium nitrite was added. The mixture was stirred for 30 minutes, after which a small amount of water was added and, the precipitate was recovered by filtration, rinsed well with water and purified by silica gel column chromatography as in Example 1. The above procedure provided the mono-, di-, tri- and tetrapalmitates which, in IR, melting point and analysis, were identical with the corresponding compounds obtained in Example 1.

EXAMPLE 4

In 20 ml of pyridine was dissolved 1 g of 2-[3-(2-chloroethyl)-3-nitrosoureido]-2-deoxy-D-gluocopyranose and a catalytic amount of p-toluenesulfonic acid was added. Under stirring at room temperature, 3.4 g of palmitic anhydride as dissolved in pyridine was added. The mixture was stirred, evaporated, ether added to the residue, filtered, the filtrate evaporated, and the residue purified. The above procedure provided the mono-, di-, tri and tetra-palmitates which, in IR, melting point and analysis, were identical with the corresponding compounds obtained in Example 1.

EXAMPLE 5

In 30 ml of dimethylformamide was dissolved 1 g of 2-[3-(2-chloroethyl)ureido]-2-deoxy-D-glucopyranose, followed by the addition of 0.15 g of potassium carbonate and 2.4 g of methyl palmitate. The reaction was conducted under mild reduced pressure at 80°–90° C. for about 6 hours, with the byproduct methanol being continuously expelled. The dimethylformamide was distilled off under reduced pressure and the insolubles were removed by extraction with two 30 ml portions of ethyl ether. The ether was distilled off, the residue was dissolved in 30 ml of acetic acid and 0.8 g of sodium nitrite powders were added under stirring at room temperature. The mixture was stirred for 30 minutes, after which time water was added and the precipitate was recovered by filtration, rinsed and dehydrated. Thereafter, the product was purified in the same manner as Example 1 to obtain the mono-, di-, and tripalmitates, together with a small amount of the tetrapalmitate.

In the same manner as above, the following compounds were synthesized.

|  | Molecular formula | m.p. | Analysis: | found % (calcd. %) | |
|---|---|---|---|---|---|
| Monocaprate | $C_{19}H_{34}ClN_3O_8$ | 111°(decomp.) | C: 48.99 (48.76) | H: 7.56 (7.32) | N: 8.88 (8.98) |
| Dicaprate | $C_{29}H_{52}ClN_3O_9$ | 103–104° | C: 55.71 (55.89) | H: 8.70 (8.41) | N: 6.87 (6.74) |
| Tricaprate | $C_{39}H_{70}ClN_3O_{10}$ | 105–106°(decomp.) | C: 60.47 (60.33) | H: 9.17 (9.09) | N: 5.53 (5.41) |
| Monolaurate | $C_{21}H_{38}ClN_3O_8$ | 109–110°(decomp.) | C: 50.71 (50.85) | H: 7.66 (7.72) | N: 8.45 (8.47) |
| Dilauate | $C_{33}H_{60}ClN_3O_9$ | 114° | C: 58.29 (58.43) | H: 8.86 (8.92) | N: 6.03 (6.19) |
| Trilaurate | $C_{45}H_{82}ClN_3O_{10}$ | 105–106°(decomp.) | C: 62.77 (62.80) | H: 9.41 (9.60) | N: 4.65 (4.88) |
| Monomyristate | $C_{23}H_{42}ClN_3O_8$ | 115–116°(decomp.) | C: 52.80 (52.71) | H: 8.35 (8.08) | N: 7.75 (8.02) |
| Dimyristate | $C_{37}H_{68}ClN_3O_9$ | 106–108° | C: 60.32 (60.51) | H: 9.63 (9.33) | N: 5.54 (5.72) |
| Trimyristate | $C_{51}H_{94}ClN_3O_{10}$ | 102–104° | C: 64.87 (64.84) | H: 10.13 (10.03) | N: 4.35 (4.45) |
| Monostearate | $C_{27}H_{50}ClN_3O_8$ | 112°(decomp.) | C: 55.84 (55.90) | H: 8.71 (8.69) | N: 6.98 (7.24) |
| Distearate | $C_{45}H_{84}ClN_3O_9$ | 101–104° | C: 63.68 (63.84) | H: 10.10 (10.00) | N: 4.77 (4.96) |
| Tristearate | $C_{63}H_{118}ClN_3O_{10}$ | 82–84° | C: 67.96 (67.98) | H: 10.91 (10.68) | N: 3.51 (3.78) |

What is claimed is:

1.

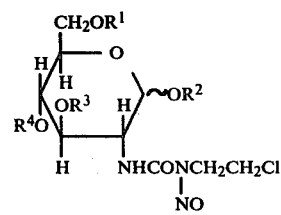

wherein $R^1$, $R^2$, $R^3$ and $R^4$ are the same or different and each is hydrogen or $-CO(C_nH_{2n})CH_3$ wherein n has a value of from 8 to 16, at least one of $R^1$, $R^2$, $R^3$ and $R^4$ being other than hydrogen.

2. A compound according to claim 1 which is the mono-, di- or tricaprate of 2-[3-(2-chloroethyl)-3-nitrosoureido]-2-deoxy-D-glucopyranose.

3. A compound according to claim 1 which is the mono-, di- or trilaurate of 2-[3-(2-chloroethyl)-3-nitrosoureido]-2-deoxy-D-glucopyranose.

4. A compound according to claim 1 which is the mono-, di- or trimyristate of 2-[3-(2-chloroethyl)-3-nitrosoureido]-2-deoxy-D-glucopyranose.

5. A compound according to claim 1 which is the mono-, di- or tristearate of 2-[3-(2-chloroethyl)-3-nitrosoureido]-2-deoxy-D-glucopyranose.

6. A compound according to claim 1 which is the mono-, di-, tri- or tetrapalmitate of 2-[3-(2-chloroethyl-3-nitro-soureido]-2-deoxy-D-glucopyranose.

* * * * *